(12) United States Patent
Barker

(10) Patent No.: US 6,925,895 B2
(45) Date of Patent: Aug. 9, 2005

(54) SAMPLE COLLECTION SYSTEM

(75) Inventor: Daniel L. Barker, Suffolk, VA (US)

(73) Assignee: Hampton Roads Sanitation District, Virginia Beach, VA (US)

( * ) Notice: Subject to any disclaimer, the term of this patent is extended or adjusted under 35 U.S.C. 154(b) by 428 days.

(21) Appl. No.: 10/189,361

(22) Filed: Jul. 2, 2002

(65) Prior Publication Data

US 2003/0004474 A1 Jan. 2, 2003

Related U.S. Application Data

(60) Provisional application No. 60/301,807, filed on Jul. 2, 2001.

(51) Int. Cl.[7] .................................................. G01N 1/00
(52) U.S. Cl. ............................... 73/864.34; 73/864.73; 73/863.31
(58) Field of Search ................................ 73/863.01, 863.02, 73/863.03, 863.11, 863.12, 863.31, 863.83, 864.73, 864.74, 864.34, 1.02

(56) References Cited

U.S. PATENT DOCUMENTS

| | | | | |
|---|---|---|---|---|
| 3,240,067 A | * | 3/1966 | Jongejan | 73/863.23 |
| 3,896,673 A | * | 7/1975 | Audouze et al. | 73/863.33 |
| 3,929,017 A | * | 12/1975 | Kowalski | 73/198 |
| 3,940,993 A | * | 3/1976 | Lapidot | 73/863.02 |
| 4,628,748 A | * | 12/1986 | Jogan et al. | 73/863.01 |
| 5,161,417 A | * | 11/1992 | Strong et al. | 73/863.86 |
| 5,237,878 A | * | 8/1993 | Hackenberg | 73/861.34 |
| 5,279,167 A | * | 1/1994 | Peterson | 73/863.86 |
| 5,708,219 A | * | 1/1998 | Scheppers et al. | 73/863.31 |
| 6,153,275 A | * | 11/2000 | Yaniger | 428/34.4 |

* cited by examiner

Primary Examiner—Robert Raevis
(74) Attorney, Agent, or Firm—George F. Helfrich

(57) ABSTRACT

A system for collecting a representative, non-contaminated sample includes a sample intake positioned in a chosen location within a body of liquid. A first conduit section transfers a sample, which has been withdrawn from the body of liquid, from the sample intake to the pump. A second conduit section transfers the sample from the pump to a receptacle for collecting the sample. The second conduit section is connected to the receptacle by means providing for an air and watertight seal for the receptacle, which is coupled with means providing for the escape of air from the receptacle during collection of the sample therein. The means providing for an air and watertight seal for the receptacle is a specially designed transfer cap.

10 Claims, 5 Drawing Sheets

SAMPLE COLLECTION SYSTEM

CROSS-REFERENCE TO RELATED APPLICATION

This application claims the benefit of U.S. Provisional Application No. 60/301,807, filed Jul. 2, 2001 for "Sample Collection System."

BACKGROUND OF THE INVENTION

1. Field of the Invention

This invention relates generally to sample collection for chemical analysis. It relates particularly to a sample collection system which provides a representative sample and which avoids contamination of the sample during collection, preparation and storage for subsequent analysis.

2. Description of the Related Art

The universally accepted maxim that a chain is no stronger than its weakest link has particular application to the procedures of chemical analysis. That is to say, all of the intricate work in conducting a qualitative and quantitative analysis will be of little value if the sample presented for this analysis is not representative of the mass from which it was obtained, and/or if such a sample was contaminated during collection, preparation, and storage.

With particular regard to the analysis of liquids, especially aqueous media such as lakes, ponds, reservoirs, rivers, and effluent streams, the analytical results obtained are often crucial. Indeed, the quality of analytical data obtained for regulatory purposes, such as derivation of site specific water quality standards, establishing wastewater permit discharge limitations, reasonable potential determinations, and in determining the compliance status of dischargers, must meet very high standards because of the legal significance of this data. In recent studies, it has been clearly demonstrated that the quality of trace metal data may be compromised because of contamination of samples during collection, preparation, and storage. Therefore, the use of clean techniques for sampling as well as analysis is critical to obtaining representative and accurate data.

Although numerous improved sampling techniques and systems have been developed over the years, today's exacting technical and legal standards required even better sampling systems for the provision of truly representative samples wherein significant contamination is eliminated.

BRIEF SUMMARY OF THE INVENTION

It is accordingly a primary object of the present invention to provide a sample collection system which affords the obtainment and storage of precisely representative samples, especially of liquids, which are essentially free of contamination.

This object is achieved, and disadvantages of related art systems are obviated by the present invention, which in essence is a closed loop sample collection system. That is to say, a sample is withdrawn, i.e., from a body of a liquid, and transferred to a collection receptacle with minimal exposure to the atmosphere and minimal exposure to solid or liquid contaminants. To ensure that the sample is representative of the mass from which it is taken, i.e., from the body of liquid, the present invention provides for the obtainment of flow-proportioned or time-weighted composite samples, as well as for grab samples and duplicate samples. The simultaneous collection of a representative, non-contaminated sample and an associated field blank is also provided by the sample collection system of the present invention.

BRIEF DESCRIPTION OF THE SEVERAL VIEWS OF THE DRAWINGS

For a more complete understanding of the present invention, including its primary object and attending benefits, reference should be made to the Detailed Description of the Invention, which is set forth below. This detailed description should be read together with the accompanying drawings, wherein.

DETAILED DESCRIPTION OF THE INVENTION

Figure 1:
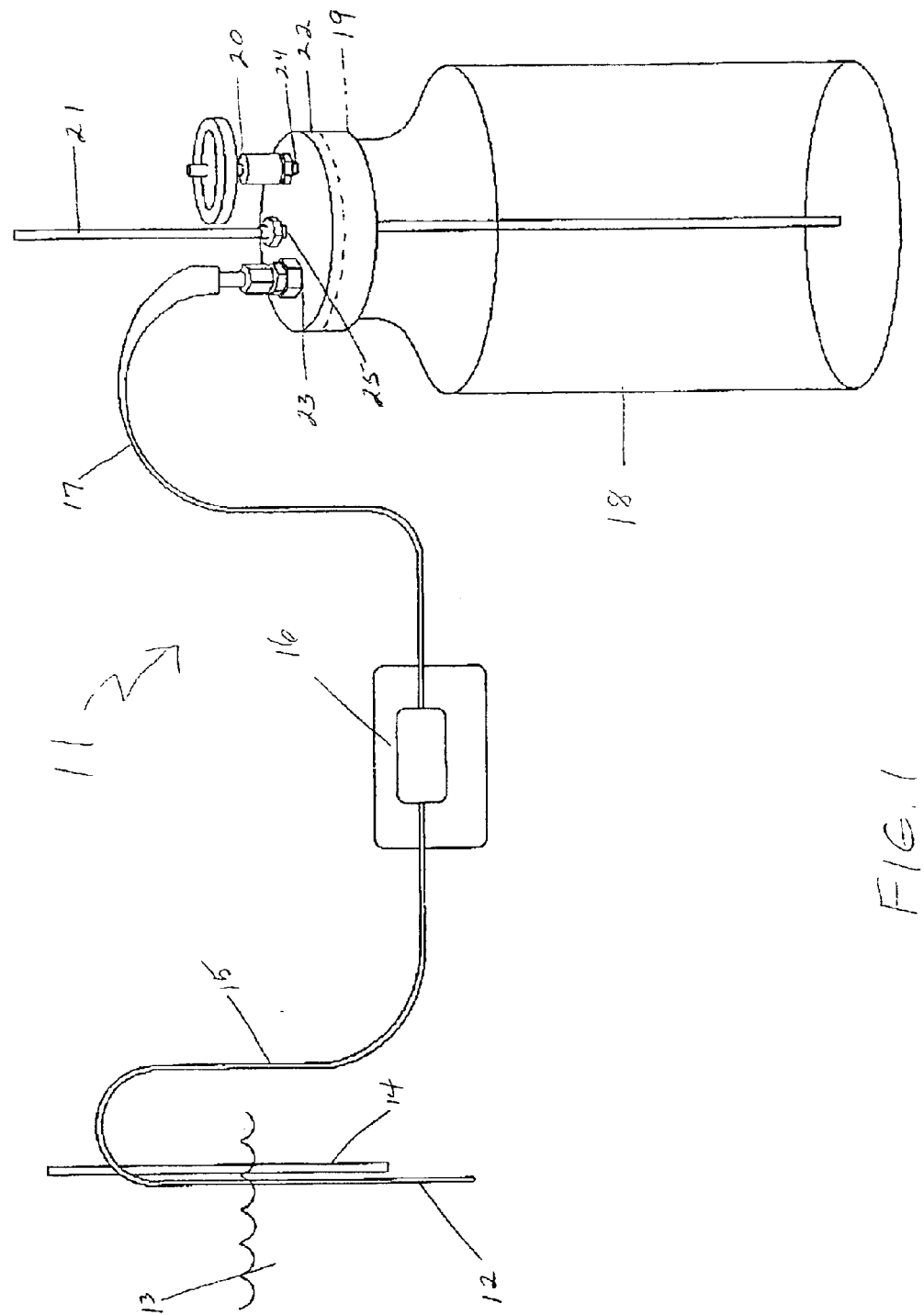
FIG. 1 is a schematic depicting a system for collecting a representative, non-contaminated sample, according to the present invention.

Referring now the drawings, FIG. 1 schematically depicts a system 11 for collecting a representative, non-contaminated sample, according to the present invention. System 11 includes a sample intake 12, which is advantageously a hollow rod or tube, which may be outfitted with a strainer, depending upon the particular liquid environment into which the sample intake is placed. For example, it may be desirable to strain or keep out large particulates, which may interfere with sample collection. The sample intake 12—as well as the conduits, receptacles, caps, tubes, and the like which are also components of the system of the present invention and which are discussed in detail hereinafter—is fabricated from a material which is inert to the liquid medium being sampled. Commonly employed for this purpose are polymeric materials such as polyethylene, polypropylene, polytetrafluoroethylene, derivatives of polytetrafluoroethylene, acetal, phenolic, and nylon. Sample intake 12 is positioned in a chosen location within body of liquid 13 by means of sample intake holder 14, which is advantageously a pole or a bracket to which sample intake 12 is attached, and which keeps sample intake 12 securely positioned in the chosen location therefor. System 11 also includes a conduit section 15, which communicates with pump 16 and sample intake 12, and conduit section 17, which communicates with pump 16 and receptacle 18 through transfer cap 19. Conduit sections 15 and 17 respectively are also fabricated from a material which is inert to the liquid medium being sampled.

Pump 16 serves to withdraw a sample from body of liquid 13 through conduit section 15 and to impel the sample through conduit section 17 into receptacle 18 through transfer cap 19. Pump 16 is advantageously an ISCO® 3710 controller, which is programmed to withdraw time-weighted or flow-proportioned composite samples of varying pre-calibrated aliquot volumes. Accordingly, sample amounts are determined by a chosen and pre-set time interval and aliquot volume, or they are determined from measurements made by a flow measuring device such as a flowmeter, which is located in the body of liquid (e.g., a moving final effluent stream) and which communicates electronically with the pump. The pump is usually powered in one of three ways: a Ni—Cd battery, a Ni—Cd battery with AC backup, or a 12V battery and battery cable. A junction box is employed in association with the pump to provide the electronic connection between the pump and external flow signals from the flow measuring device, thereby providing flow-proportioned composite sampling when appropriate. The pump 16 is also capable of providing a grab sample, as discussed in more detail hereinafter.

Receptacle 18 serves as a collection container for the sample. It is also fabricated from a material which is inert to the liquid being sampled. The sample enters receptacle 18 from conduit section 17 through transfer cap 19, which provides an air and watertight seal for receptacle 18. That is to say, there is no leakage of air or water through transfer cap 19, which is an integral part of the instant closed loop sample collection system. A vent 20 is provided in transfer cap 19, which is an integral part of the instant closed loop sample collection system. A vent 20 is provided in transfer cap 19 to provide for the escape of air from receptacle 18 during collection of the sample therein. Vent 20 may be coupled with a filter if desired. Pickup tube 21 is provided for manipulating the sample, e.g., for removing a portion of the sample for analysis, without removing transfer cap 19. Pickup tube 21 is a tube made of inert material which passes through transfer cap 19 into receptacle 18 and extends to the bottom of receptacle 18. The sample is accordingly collected by the sample collection system of the present invention and manipulated, as appropriate, without any significant contamination internally or from the outside atmosphere during collection and manipulation.

Transfer cap 19, which is advantageously a screw cap, has a roof 22 of sufficient thickness to provide a positive and permanent connection for conduit section 17 and for vent 20, as well as for pickup tube 21. That is to say, the inert fitting connections to transfer cap 19 at 23, 24 and 25 respectively are precise—i.e., allowing no leakage—and durable—i.e., not deteriorating with the passage of time. Without a sufficient thickness of roof 22, some leakage will take place, especially with the passage of time. A sufficient thickness for roof 22 is determined empirically, and is dependent upon the size and configuration of transfer cap 19 and the material from which it is fabricated among other variables. Roof thicknesses of standard screw caps have been generally determined to be insufficient to provide the positive and permanent connections required for the sample collection system according to the present invention. Therefore transfer caps 19 are specially fabricated so that the roofs 22 thereof have been augmented to provide the necessary additional thickness. Without such a thickness augmentation, leakage around the connections will take place, especially with the passage of time. As an example of a preferred embodiment, a roof thickness of from about ⅝ inches to ⅞ inches has been found sufficient when the transfer cap 19 is fabricated from high molecular weight polyethylene. The transfer cap 19 is fabricated from a rigid, non-metallic material, especially a polymeric material, preferably by machining or injection molding. The polymeric material is desirably a member selected from the group consisting of polytetrafluoroethylene, derivatives of polytetrafluoroethylene, acetal, phenolic, polypropylene, nylon, and polyethylene, with high molecular weight polyethylene being especially preferred for many applications.

Figure 2:
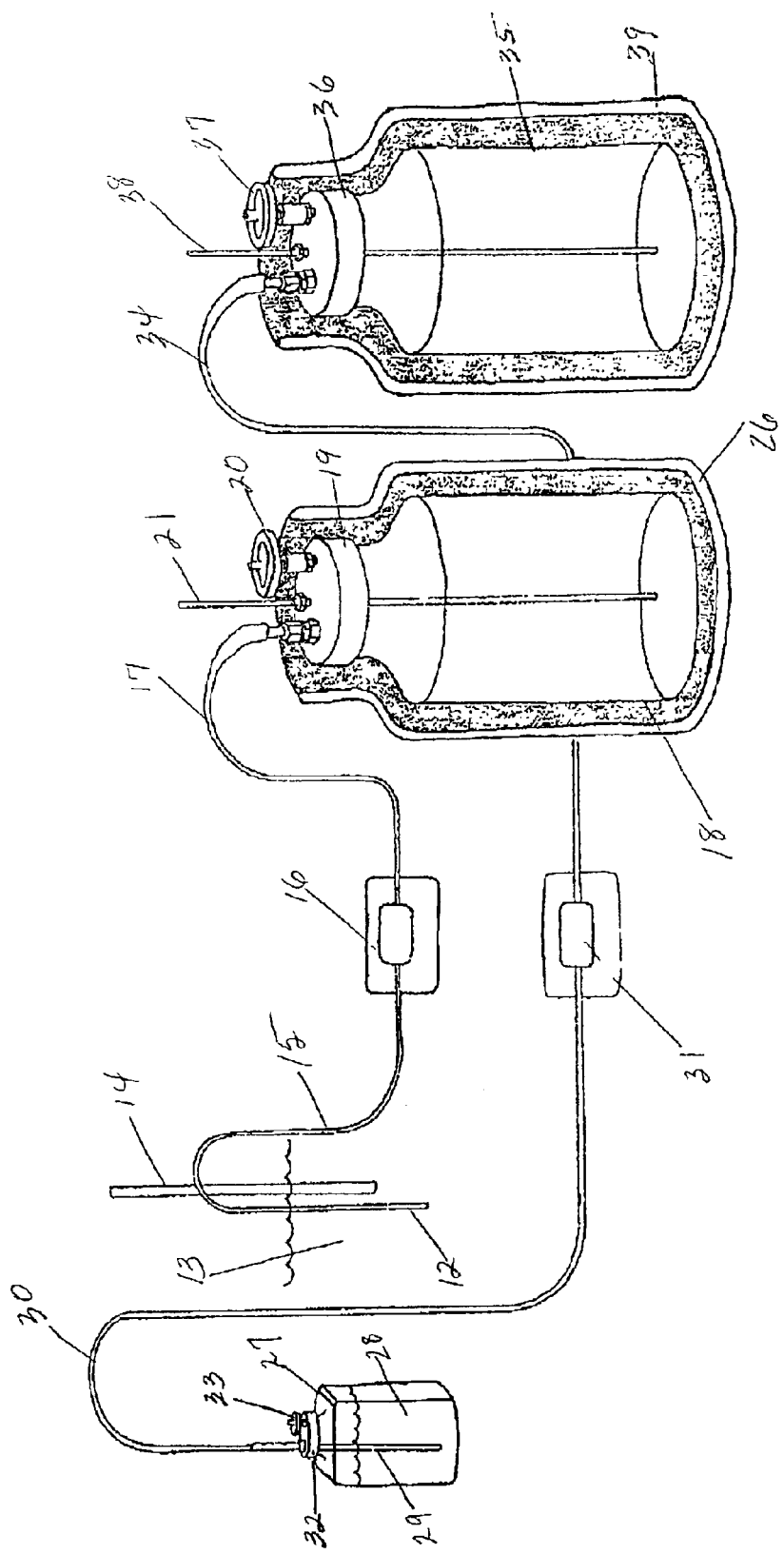
FIG. 2 is a schematic depicting a system for simultaneously collecting a representative, non-contaminated sample and an associated field blank, according to the present invention.

Referring now to FIG. 2, depicted therein is a system for simultaneously collecting a representative, non-contaminated sample and an associated field blank, according to the present invention. Sample intake 12 is positioned in a chosen location within body of liquid 13 by means of sample intake holder 14. Conduit section 15 communicates with pump 16 and sample intake 12, and conduit section 17 communicates with pump 16 and receptacle 18 through transfer cap 19 which is outfitted with vent 20 and pickup tube 21. [Sample intake 12, sample intake holder 14, first conduit section 15, pump 16, second conduit 17, receptacle 18, transfer cap 19, vent 20, and pickup tube 21, as referred to hereat and in additional embodiments presented hereinbelow, are as disclosed in detail hereinabove.] It has been found advantageous, and even required in some instances, to maintain the collected sample at a given temperature. Under these circumstances the instant invention includes means 26 communicating with receptacle 18 for maintaining the collected sample at a chosen temperature. Such means includes a common cooler which has been filled with small plastic bags containing ice. Use of such a cooler maintains the sample at a temperature of 4° C. or below. The present embodiment of the sample collection system according to the present invention also includes a vessel 27 for holding analyte-free water 28, and means 29 for connecting conduit section 30 to pump 31, whereby an analyte-free water specimen is simultaneously withdrawn from vessel 27 to pump 31 through an air and watertight seal for vessel 27, which is provided by transfer cap 32. Transfer cap 32 is outfitted with a vent 33, which is optionally coupled with a filter. Pump 31 withdraws a specimen of analyte-free water through conduit section 30, and impels the analyte-free water specimen through conduit section 30, and impels the analyte-free water specimen through conduit section 34 to receptacle 35 through transfer cap 36, which provides an air and watertight seal for receptacle 35 and is coupled with vent 37, which provides for the escape of air from vessel 35 during collection of the analyte-free water specimen therein. Pickup tube 38 allows for manipulation of the specimen of analyte-free water which has been collected in receptacle 35 without removing transfer cap 36, and means 39 communicates with receptacle 35 for maintaining the collected specimen of analyte-free water at a chosen temperature. In this embodiment the following groupings of elements are equivalent in construction and function: sample intake 12 and means 29; conduit sections 15 and 30; pumps 16 and 31; conduit sections 17 and 34; receptacles 18 and 35; means 26 and 39; transfer caps 19, 32, and 36; vents 20, 33, and 37; and pickup tubes 21 and 38. The specimen of analyte-free water which has been collected hereby is referred to as a field blank, as it is collected at the sampling site simultaneously with, and in identical fashion to the collection of the sample of the body of liquid. Field blanks are the most comprehensive of all blanks because they are collected as actual samples, and they are treated as actual samples inclusive of all site conditions, handling, preservation, transport, and analysis. In order to ensure an identical withdrawal of the actual sample and the field blank from their respective sources, a junction box communicates with pumps 16 and 31 and sends signals thereto ensuring their identical activation.

Figure 3:
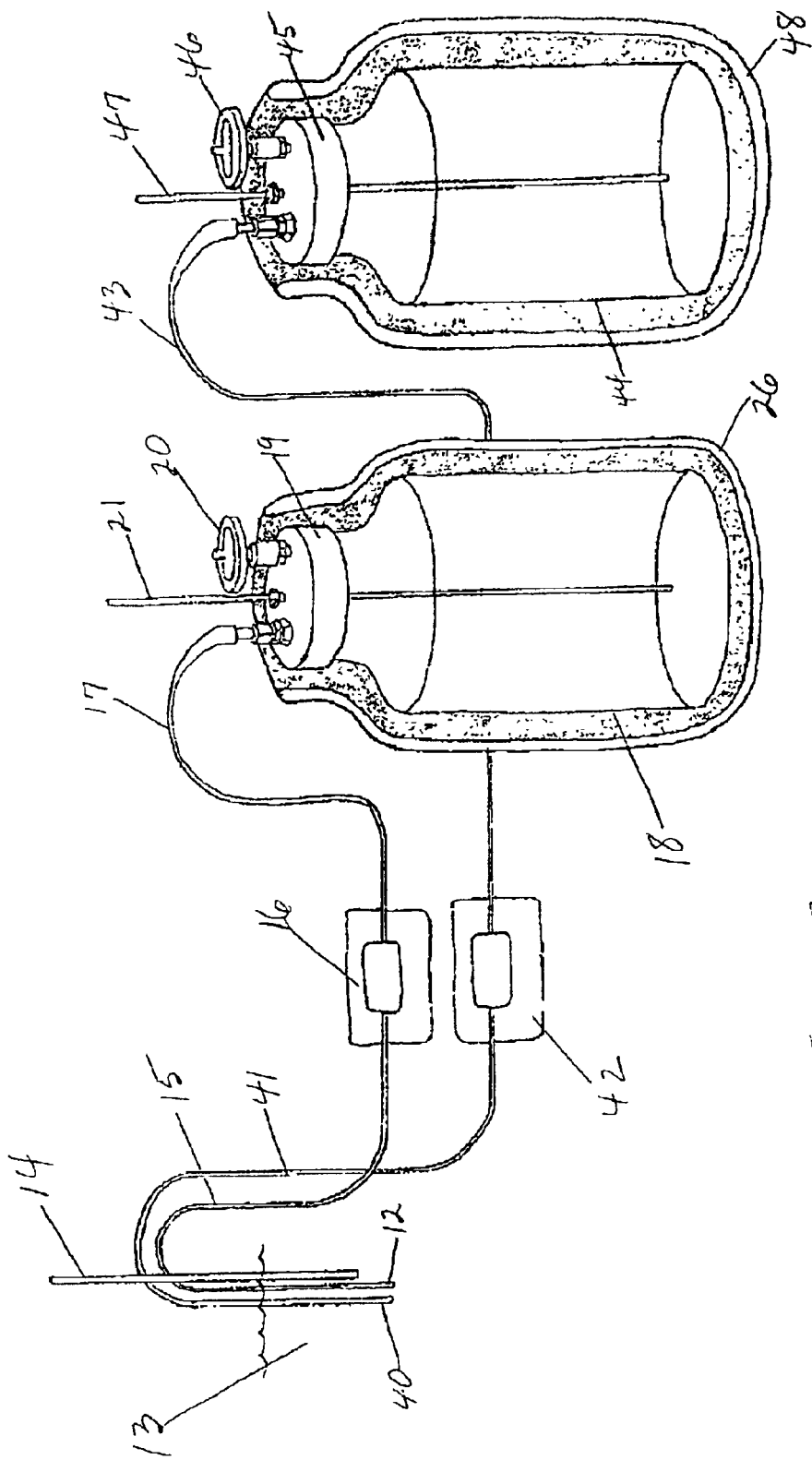
FIG. 3 is a schematic depicting a system for simultaneously collecting a representative, non-contaminated sample and an associated duplicate sample, according the present invention.

Referring now to FIG. 3, depicted therein is a system for collecting a representative, non-contaminated sample, and an associated field duplicate sample. In this embodiment a sample is withdrawn by sample intake 12, which is positioned by sample intake holder 14, and passed through conduit section 15 to pump 16, whence it is impelled through conduit section 17 into receptacle 18 through transfer cap 19, which is outfitted with vent 20 and pickup tube 21. Receptacle 18 communicates with means 26 for maintaining the sample collected in receptacle 18 at a chosen temperature. Simultaneously therewith, a duplicate sample is withdrawn by sample intake 40, which is positioned by sample intake holder 14, and passed through conduit section 41 to pump 42, whence it is impelled through conduit section 43 into receptacle 44 through transfer cap 45, which is outfitted with vent 46 and pickup tube 47. Receptacle 44 communicates with means 48 for maintaining the duplicate sample collected in receptacle 44 at a chosen temperature. A junction box communicates with pumps 16 and 42 and sends signals thereto ensuring their identical activation. In this embodiment the following pairs of elements are identical in construction and function: sample intakes 12 and 40; conduit sections 15 and 41; pumps 16 and 42; conduit sections 17 and 43; receptacles 18 and 44; transfer caps 19 and 45; vents 20 and 46; pickup tubes 21 and 47; and means 26 and 48.

In the preceding embodiments, details have been presented concerning the obtainment of: a composite sample, a composite sample and an associated field blank, and a composite sample and an associated field duplicate sample. That is to say, the samples, blanks, and duplicates have been time-weighted or flow-proportioned composites, as described hereinabove. As understood by the skilled artisan, the sample collection system of the present invention is also applicable to the obtainment of grab samples and field blanks, i.e., those samples and field blanks which are obtained by instantaneous withdrawal of a sample from a body of liquid and instantaneous withdrawal of a specimen of analyte-free water from a vessel containing the same. Such grab samples and grab field blanks provide in effect a snapshot picture of exactly what is present at a particular point in time in the liquid medium.

Figure 4:
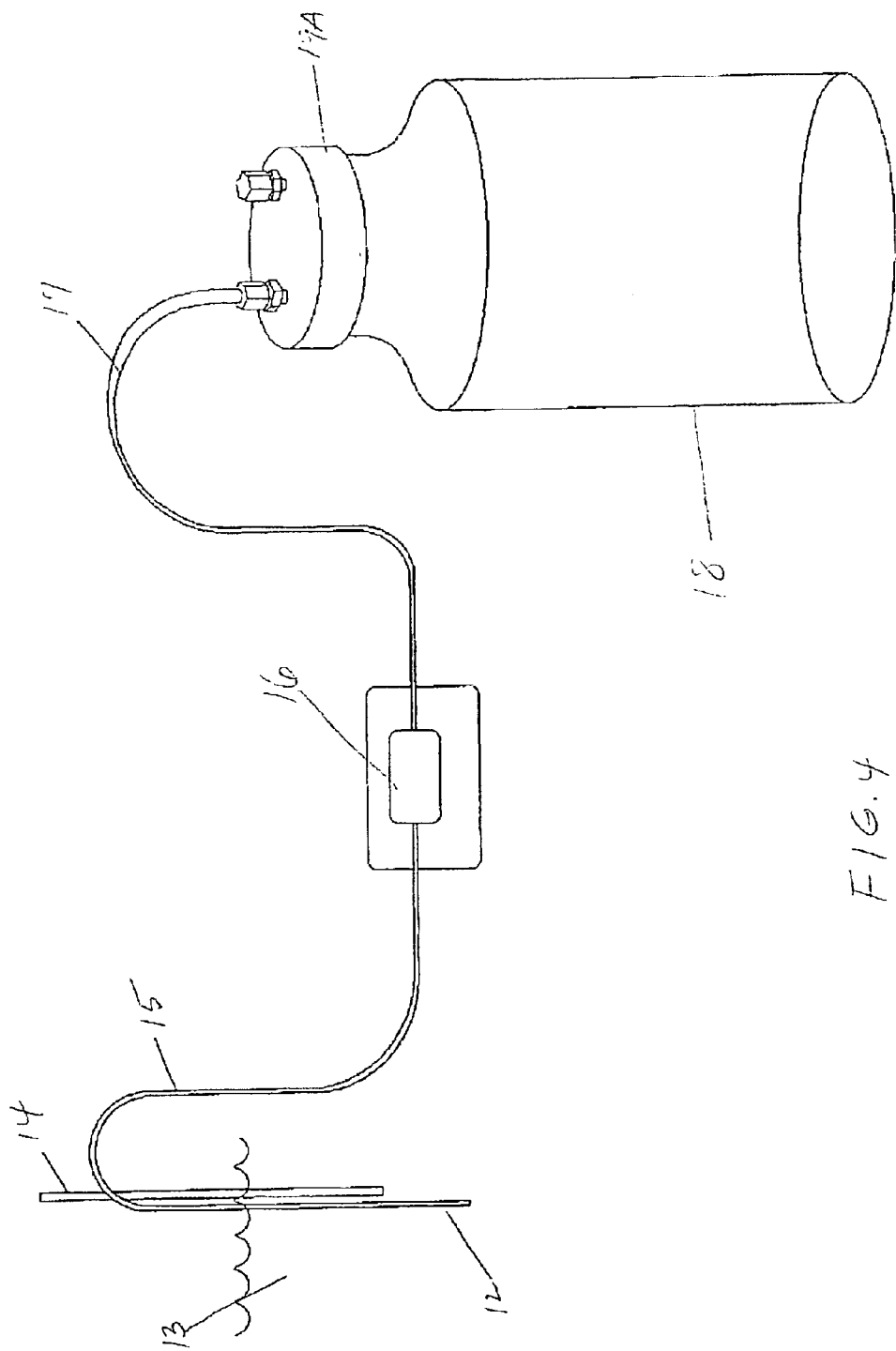
FIG. 4 is a schematic depicting a system for collecting a grab sample, according to the present invention.
Figure 5:
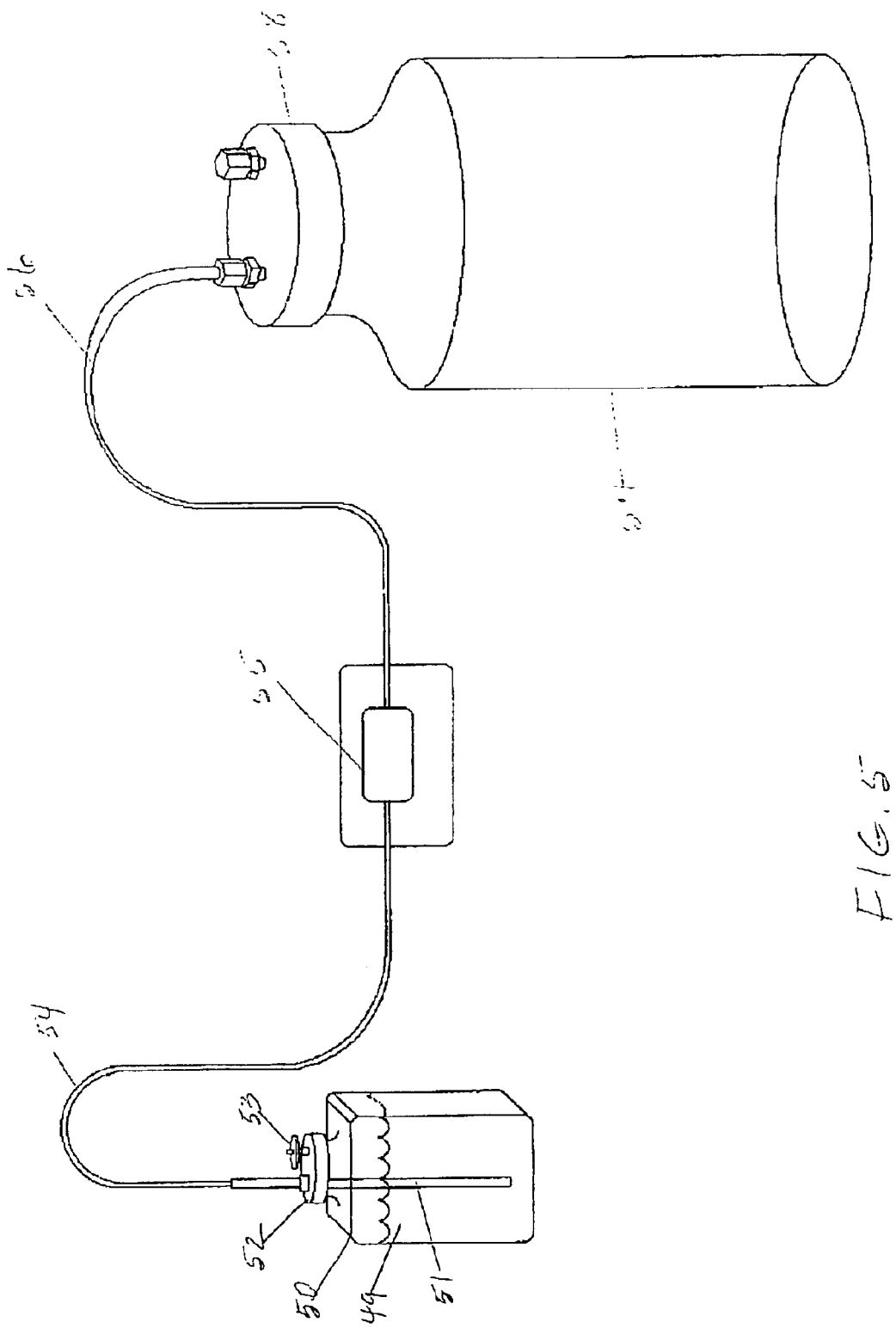
FIG. 5 is a schematic depicting a system for collecting a grab field blank, according to the present invention.

FIGS. 4 and 5 depict sample collection systems according to the present invention for the obtainment of a grab sample and a grab field blank respectively. Referring now to FIG. 4, a sample from body of liquid 13 is instantaneously withdrawn by pump 16 from sample intake 12 through conduit section 15, whence it is impelled by pump 16 through conduit section 17 into receptacle 18 through transfer cap 19A. Transfer cap 19A is identical to transfer cap 19 of the embodiments specified hereinabove, except that no vent is provided for the escape of air from receptacle 18 and no pickup tube is provided for manipulation of the sample collected. Such a vent and pickup tube have been found to be unnecessary in this application, because of the relatively small amount of sample obtained.

Referring now to FIG. 5, a specimen of analyte-free water from the analyte-free water 49 contained in vessel 50 is instantaneously withdrawn by means of pump 55 from sample intake 51 in vessel to through transfer cap 52, having vent 53 located therein, and thence through conduit section 54. Pump 55 then impels the specimen of analyte-free water through conduit section 56 into receptacle 57 through transfer cap 58. The following pairs of elements from FIGS. 4 and 5 are identical in construction: sample intakes 12 and 51; conduit sections 15 and 54; pumps 16 and 55; conduit sections 17 and 56; receptacles 18 and 57; and transfer caps 19A and 58. Vessel 50 of FIG. 5 is identical to vessel 27 of FIG. 2; and transfer cap 52 of FIG. 5 with its associated vent 53 is identical to transfer cap 32 of FIG. 2 with its associated vent 33.

The sample collection system of the present invention has found special application in the evaluation of the final effluent metals levels during normal operating conditions of various industrial plants.

The present invention has been described in detail with respect to certain preferred embodiments thereof. It is understood that variations and modifications in this detail may be made without any departure from the spirit and scope of the present invention, as defined in the hereto-appended claims.

I claim:

1. A system for simultaneously collecting a representative, non-contaminated sample and an associated field blank, which system comprises:

(a) A sample intake;

(b) Means for positioning the sample intake in a chosen location within a body of liquid;

(c) A first conduit section for transferring a sample, which has been withdrawn from the body of liquid, from the sample intake to a first pump;

(d) A second conduit section for transferring the sample from the first pump to a first receptacle for collecting the sample;

(e) Means for connecting the second conduit section to the first receptacle to provide an air and watertight seal for the first receptacle, coupled with means for providing for escape of air from the first receptacle during collection of the sample therein;

(f) A vessel for holding analyte-free water;

(g) Moans for connecting a third conduit section to the vessel for holding analyte-free water to allow an analyte-free water specimen to be withdrawn from the vessel to a second pump through an air and watertight seal for the vessel;

(h) A fourth conduit section for transferring the analyte-free water specimen from the second pump to a second receptacle for collecting the analyte-free water specimen; and (i) Means for connecting the fourth conduit section to the second receptacle to provide an air and watertight seal for the second receptacle, coupled with means for providing for the escape of air from the second receptacle during collection of the analyte-free water specimen therein.

2. The system of claim 1, which additionally comprises means communicating with the first receptacle for maintaining the sample at a chosen temperature, and means communicating with the second receptacle for maintaining the analyte-free water specimen at a chosen temperature.

3. The system of claim 1, wherein the means for connecting the second conduit section to die first receptacle to provide an air and watertight seal for the first receptacle is a transfer cap; and wherein the means for connecting the third conduit section to the vessel for holding analyte-free water is a transfer cap; and wherein the means for connecting the fourth conduit section to the second receptacle is a transfer cap; the transfer cap in each case being fabricated to provide an air and watertight seal for the first receptacle, the vessel for holding analyte-free water, and the second receptacle. respectively; the transfer cap in each case possessing a roof having a thickness which is sufficient to provide a permanent and positive connection for the second conduit section, and for the fourth conduit section, respectively, as well as for the means providing for the escape, intake, and escape of air during collection, withdrawal, and collection, respectively.

4. The system of claim 3, wherein each transfer cap is fabricated from a rigid, non-metallic material.

5. The system of claim 4, wherein the rigid, non-metallic material is a polymeric material.

6. The system of claim 5, wherein the polymeric material is a member selected from the group consisting of polytetrafluoroethylene, derivatives of polytetrafluoroethylene, acetal, phenolic, pholpropylene, polyethylene, and nylon.

7. The system of claim 6, wherein the polymeric material is high molecular weight polyethylene.

8. The system of claim 4, wherein each transfer cap is fabricated by machining or injection molding.

9. The system of claim 1, wherein the sample is a flow-proportioned or time-weighted composite sample.

10. The system of claim 1, wherein the sample is a grab sample.

* * * * *